United States Patent
Averbuch

(10) Patent No.: US 11,315,323 B2
(45) Date of Patent: Apr. 26, 2022

(54) CONTROLLED PERSPECTIVE GUIDANCE METHOD

(71) Applicant: COVIDIEN LP, Mansfield, MA (US)

(72) Inventor: Dorian Averbuch, Ramat HaSharon (IL)

(73) Assignee: COVIDIEN LP, Mansfield, MA (US)

( * ) Notice: Subject to any disclaimer, the term of this patent is extended or adjusted under 35 U.S.C. 154(b) by 309 days.

(21) Appl. No.: 16/538,299

(22) Filed: Aug. 12, 2019

(65) Prior Publication Data

US 2019/0362552 A1 Nov. 28, 2019

Related U.S. Application Data

(66) Continuation of application No. 12/369,466, filed on Feb. 11, 2009, now Pat. No. 10,388,066, Substitute for application No. 61/028,098, filed on Feb. 12, 2008.

(51) Int. Cl.
*G06T 19/00* (2011.01)
*A61B 34/20* (2016.01)
*A61B 5/06* (2006.01)
*A61B 1/00* (2006.01)

(52) U.S. Cl.
CPC ............ *G06T 19/003* (2013.01); *A61B 5/066* (2013.01); *A61B 34/20* (2016.02); *A61B 1/00009* (2013.01); *A61B 5/065* (2013.01); *A61B 2034/2051* (2016.02)

(58) Field of Classification Search
None
See application file for complete search history.

(56) References Cited

U.S. PATENT DOCUMENTS

| | | |
|---|---|---|
| 6,346,940 B1 | 2/2002 | Fukunaga |
| 10,388,066 B2 | 8/2019 | Averbuch |
| 2002/0049375 A1 | 4/2002 | Strommer et al. |
| 2004/0122310 A1 | 6/2004 | Lim |
| 2005/0182295 A1 | 8/2005 | Soper et al. |
| 2006/0100505 A1 | 5/2006 | Viswanathan |
| 2007/0052724 A1 | 3/2007 | Graham et al. |
| 2007/0265639 A1 | 11/2007 | Danek et al. |
| 2008/0008368 A1 | 1/2008 | Matsumoto |

FOREIGN PATENT DOCUMENTS

| | | |
|---|---|---|
| EP | 1391181 A1 | 2/2004 |
| EP | 1466552 A1 | 10/2004 |
| WO | 2006121974 A2 | 11/2006 |

OTHER PUBLICATIONS

"Evaluation of a Virtual Endoscopy Simulator for Training in Gastrointestinal Endoscopy" by A. Ferlitsch et al. Endoscopy. 34:698-702 (2002.).

(Continued)

*Primary Examiner* — Jason M Ip
(74) *Attorney, Agent, or Firm* — Weber Rosselli & Cannon LLP

(57) ABSTRACT

Navigation through a network of body passages, such as through the airways, is improved by a method of displaying information which provides a fly-through visualization of the passageway. As landmarks or waypoints are passed, the view changes to a next segment in a planned pathway to a target. Such a visualization technique avoids tunnel vision, such as that encountered while using real-time endoscopes.

20 Claims, 11 Drawing Sheets

(56) References Cited

OTHER PUBLICATIONS

Tele-training simulation for the surgical robot system "da Vinci" by S. Suzuki et al. Int Cong Ser. 1268 (2004) 86-91.
International Searching Authority/U.S. Receiving Office, International Search Report in International Application No. PCT/IB09/00238, dated Jul. 14, 2009, 8 pages.
European Office Action, Application No. 13 168 297.3 dated Mar. 27, 2015.
European Office Action issued in corresponding EP 13168288 dated Feb. 2, 2015.
European Search Report issued in European Patent Application No. EP15185151 dated May 31, 2016, 7 pages.

CONTROLLED PERSPECTIVE GUIDANCE METHOD

RELATED APPLICATIONS

This application is a continuation of U.S. application Ser. No. 12/369,466, filed Feb. 11, 2009, which claims priority to U.S. Provisional Application Ser. No. 61/028,098 filed Feb. 12, 2008 entitled Controlled Perspective Guidance Method, which is hereby incorporated herein by reference.

BACKGROUND OF THE INVENTION

Identifying and treating lung tissue abnormalities presents challenges that are somewhat unique to the lungs. If a tissue lesion or tumor is to be identified and excised surgically, the chest wall must be opened to provide access to the lungs. Opening the chest wall is a common procedure but one that presents risks of infection and lengthy recovery time, nonetheless.

A desirable alternative to surgery, in terms of reducing patient trauma, is to identify and excise the tumor endoscopically. Endoscopic surgery in the lungs, however, means that the complicated bronchial maze must be navigated. Endoscopes have cameras at their distal tips that provide a physician a real-time image through the end of the endoscope while the endoscope is being advanced through the bronchial system. However, typical endoscopes are too wide to be advanced deep into the lungs as the diameters of the airways decrease toward the alveoli.

In order to assist in navigating deep in the lungs, systems have been developed that include a sensor at the distal tip of a probe. The sensor interacts with a field generator to provide a real-time indication of its location in a three-dimensional space encompassing the lungs. The real-time indication is superimposed on a computer image of the bronchial tree (known as a "virtual bronchial tree") so that the location indication generated by the sensor is useful to the physician.

Heretofore, the location data has been presented to the physician as though the sensor is actually an endoscope. Hence, the virtual bronchial tree image is presented from the perspective of the tip of the sensor and as the sensor is advanced, the image of the virtual bronchial tree moves past the sides of the sensor and disappears.

The difficulty when viewing navigation progress in this manner, as is true with an endoscope as well, is that the physician has tunnel vision. No peripheral vision is available. Thus, if the end of the sensor is adjacent a branch, the branch may not appear on the screen. The physician wanting to see to the sides of the endoscope or, in the virtual sense, the sensor, must either retract the probe or turn it in the direction of the branch.

This visualization problem becomes even more confusing when considering first that the sensor is moving with the cardiac rhythm and breathing cycle of the patient and second that the sensor often twists when the steering mechanism is activated. The cardiac rhythm and breathing cycle cause jittering of the virtual image, which can be very disorienting. With regards to the use of the steering mechanism, most steerable probes have a tip that can be turned in one to four directions. This means that in order to turn the tip in a desired direction, it may be necessary to rotate the tip around its longitudinal axis up to 180 degrees prior to deflection. This will cause the image being viewed to flip and then turn. The physician can easily become disoriented after a few turns while trying to navigate to a lesion. There is a need to provide more useable data display for use in navigating a probe through a virtual bronchial tree.

SUMMARY OF THE INVENTION

The system and method of the present invention provides more useable visual presentation to a physician using an intra-body navigation system. Generally, the system and method of the present invention uses a system of planned waypoints along a planned route through the bronchial tree in order to incrementally advance the image presented to the physician.

Thus, a physician using the system and method of the present invention will see an image of the bronchial tree and an image of the sensor being advanced through the airways to a subsequent waypoint. Once the sensor has reached the next waypoint and has been turned down an appropriate branch, the image perspective will be advanced to that next waypoint. Rather than the images being presented as though there were a camera mounted on the sensor, which may be moving in a chaotic, erratic fashion, the images of the virtual bronchial tree are presented in a controlled manner, for example as though cameras are mounted on each of the waypoints.

In one embodiment, rhythmic movement (movement caused by the breathing cycle, cardiac cycle, or patient movement) is visualized by tying the perspective of the video image to the visible portion of the bronchial tree such that there is no viewable relative movement between the "camera" and the bronchial tree. Rather, all rhythmic movement is visualized by showing movement of the probe. Hence, if the bronchial tree moves in such a manner that it affects the relative position of the probe within the airways, the probe is seen as moving. This provides the physician with a more accurate perception of the location of the probe.

In another embodiment, calculations and visualization are simplified by incorporating the reality that while the probe is being advanced through a section of the airways that contains no branches, the probe will be automatically guided by the sidewalls of the airway. Hence, no particularly useful information is gleaned from an image that is showing rhythmic movement. In this embodiment, a simplified view of the sensor being advanced through the center of the airway is provided until the sensor reaches a fork. Once the fork is reached, the probe will be shown as veering down one of the available branches. In this way, the physician knows which branch the probe has entered. A preferred aspect of this embodiment provides a highlighted representation of the target branch, as determined in a pre-operative planning stage.

In another embodiment, the airway is represented by a simple tunnel with the next waypoint or branch highlighted somehow. As the probe is advanced, the highlighted waypoint increases in size to simulate getting closer. As the probe appears to pass the highlighted waypoint, the view switches, either manually or automatically, to a new airway with the next waypoint highlighted in the distance.

In yet another aspect of the present invention, an overlay or second window is displayed giving a schematic diagram of the bronchial tree and the entire path to the target shown. Preferably, an indication of the present sensor location is shown, thereby providing the physician with an indication of the probe's progress towards the target.

DETAILED DESCRIPTION OF THE INVENTION

Figure 1:
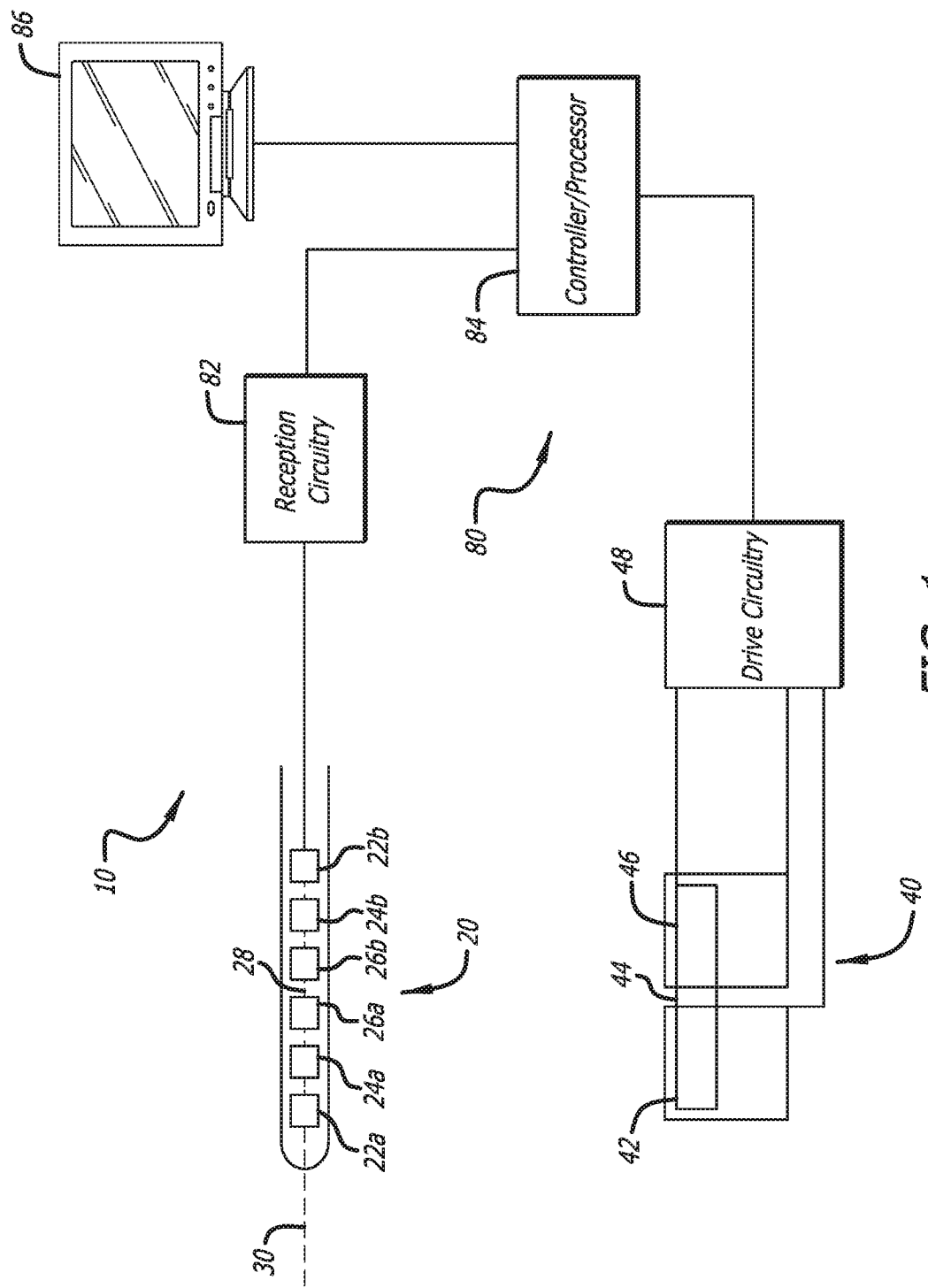
FIG. 1 is a diagram of an example of a location system that may be used with the present invention.

Referring now to the figures and first to FIG. 1, there is shown a location system 10. Though the navigation display system and method of the present invention may be used with any location system having virtual capabilities, a description of a location system 10 is provided by way of example.

The location system 10 generally includes a locatable guide 20, a location board 40, and a control system 80. The locatable guide 20 is a probe having a receiver that generally includes a plurality of (preferably three) field component sensors 22, 24 and 26. Each of the field sensor components is arranged for sensing a different component of an electromagnetic field generated by the location board 40.

The location system 10 also includes the location board 40. The location board 40 is a transmitter of electromagnetic radiation. The location board 40 includes a stack of three substantially planar rectangular loop antennas 42, 44 and 46 connected to drive circuitry 48. Drive circuitry 48 includes appropriate signal generators and amplifiers for driving each of the loop antennas 42, 44 and 46 at their corresponding frequencies. The electromagnetic waves generated by the location board 40 are received by the locatable guide 20 and converted into electrical signals that are then sent to the control system 80.

The control system 80 generally includes reception circuitry 82 and a display 86. The reception circuitry has appropriate amplifiers and A/D converters. The reception circuitry 82 and the driving circuitry 48, which may be considered part of the control system 80, are controlled by a controller/processor 84 that typically is an appropriately programmed computer. The controller/processor 84 directs the generation of transmitted signals by driving circuitry 48. The controller/processor 84 also generates video signals, which are sent to the display 86.

Having introduced the basic system 10 on which the present invention is practiced, attention can now be focused on the manner in which the controller/processor 84 presents information on the display 86.

Figure 2:
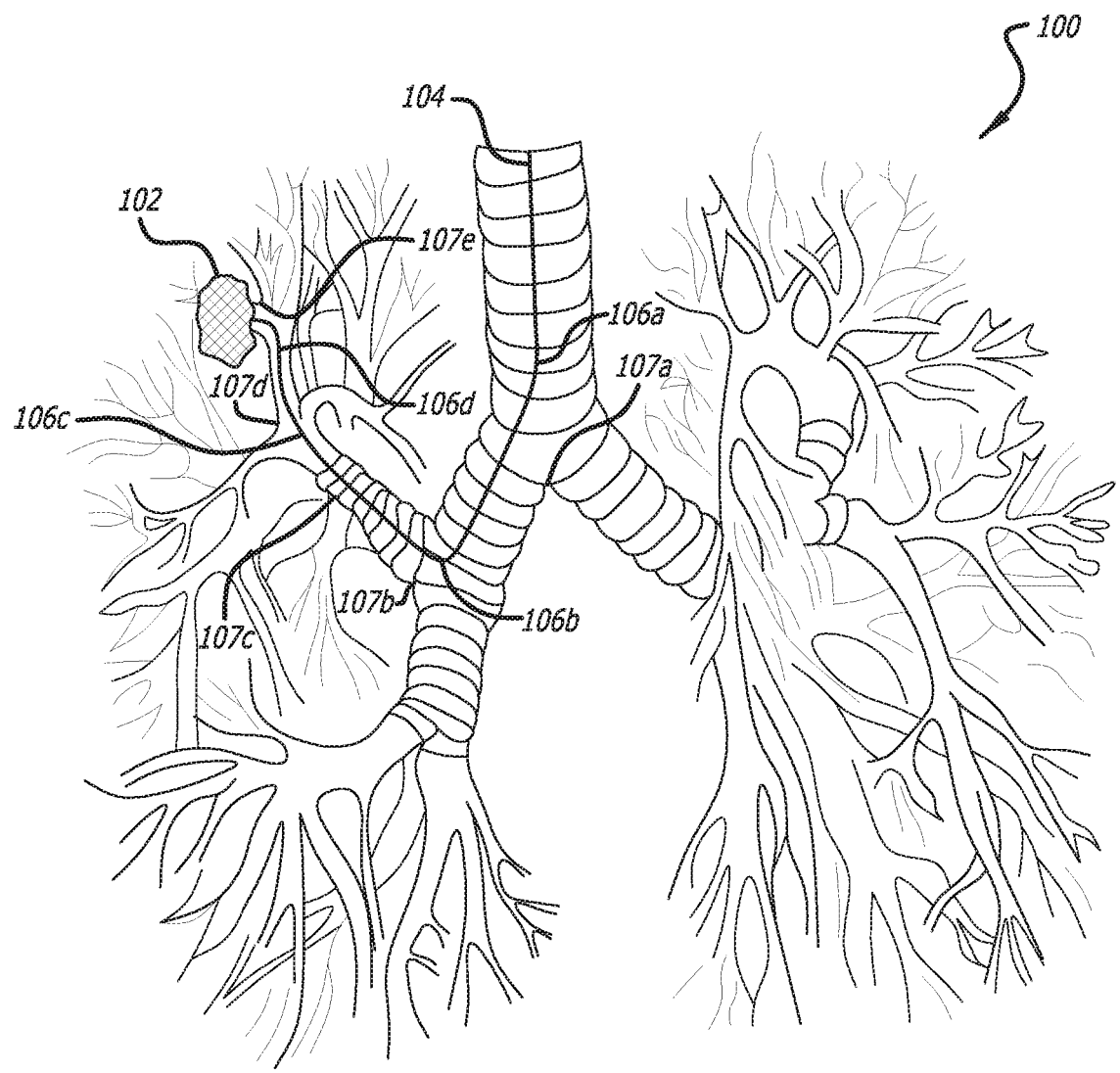
FIGS. 2-22 are examples of displayed images of the present invention.

Preferably, all of the embodiments of the present invention have the ability to display an overview of the bronchial tree. This overview may be obtained from subjective sources such as CT images or objective sources such as medical atlases, etc. An example of such an overview 100 is provided in FIG. 2. The overview 100 may be displayed on a split screen or on a separate monitor. The overview may also be presented in a separate window on the display 86 but it is likely that a physician would benefit from being able to constantly monitor the overview 100. The overview 100 includes an indication of a targeted lesion 102 and a path 104 to the lesion 102. The path 104 is determined in a preoperative planning stage, either manually or automatically, or a combination thereof (semi-automatically, for example).

The path 104 includes a plurality of waypoints or turning points 106a-d enroute to the lesion 102. Navigation to these waypoints 106a-d is supplemented by identifiable anatomical landmarks 107a-e, typically bifurcations, trifurcations, or forks.

During navigation to the target lesion 102, an virtual interior view of the airway will be displayed along with the overview 100. This interior view may be realistic, constructed from CT scans, for example, or may be very basic (schematic). Additionally, this may be presented as a perspective or parallel geometric view (i.e. with or without a vanishing point). Hence, in a preferred embodiment, FIGS. 3, 5, 7, 9, 11, 13, 15, and 17-22 show an interior display which will be presented with the overview 100. Various embodiments of the present invention will be demonstrated using the same path 104 and target lesion 102 from FIG. 2.

Figure 3:
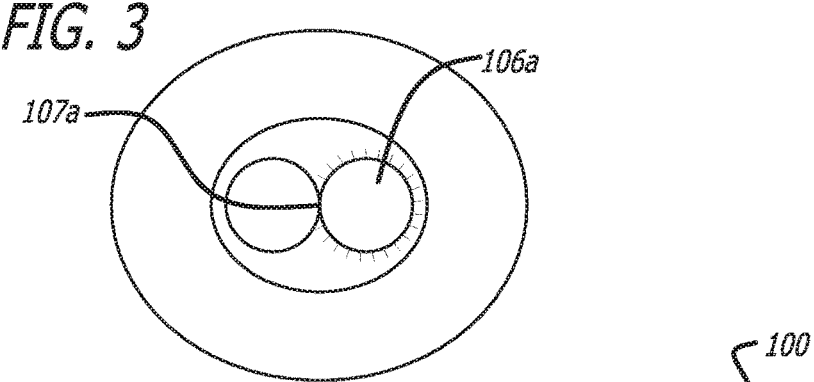
Figure 4:
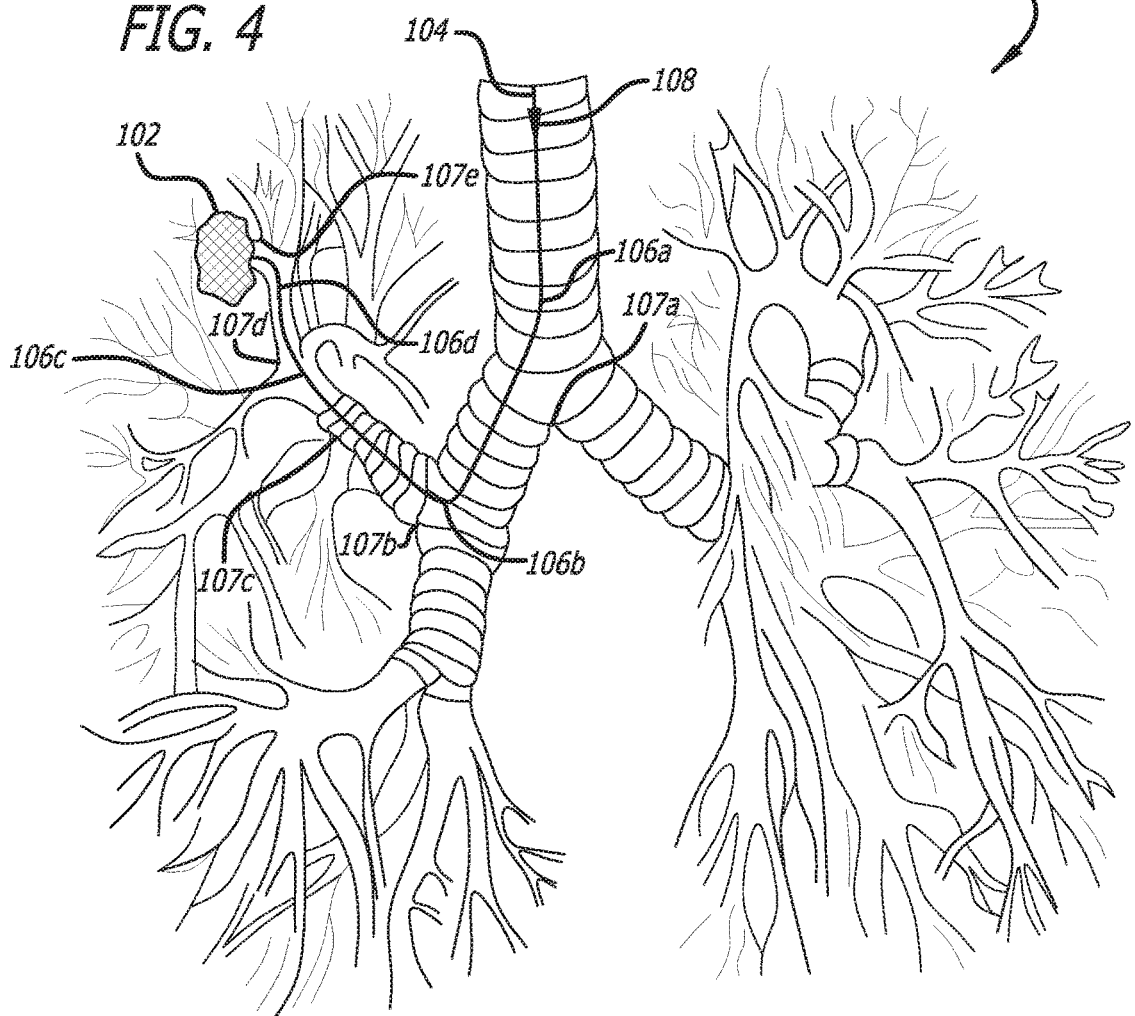

A first embodiment is shown in FIGS. 3-16. In this embodiment, the display is shown from a viewpoint just over or beyond the distal tip of the locatable guide. The display remains centered in the airway and does not twist or otherwise move with the movement of the locatable guide except in an axial direction. FIG. 3 shows the first landmark 107a and the first waypoint 106a. Because the waypoints are turning points and not (necessarily) physical landmarks, the waypoints may be displayed as suspended points that indicate to the physician that upon reaching the waypoint, the physician needs to steer the probe in the next direction. Alternatively, the waypoints need not be displayed. In order to ease navigation, the correct airway will be highlighted somehow, as shown. Optionally, the highlighted airway could change color or blink when the probe reaches the waypoint to indicate a direction change is needed. To further assist with navigation, the position of the locatable guide is shown as an arrowhead 108, or some other indication, on the overview 100 as shown in FIG. 4.

Figure 5:
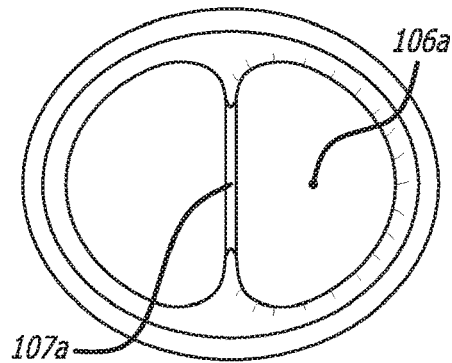
Figure 6:
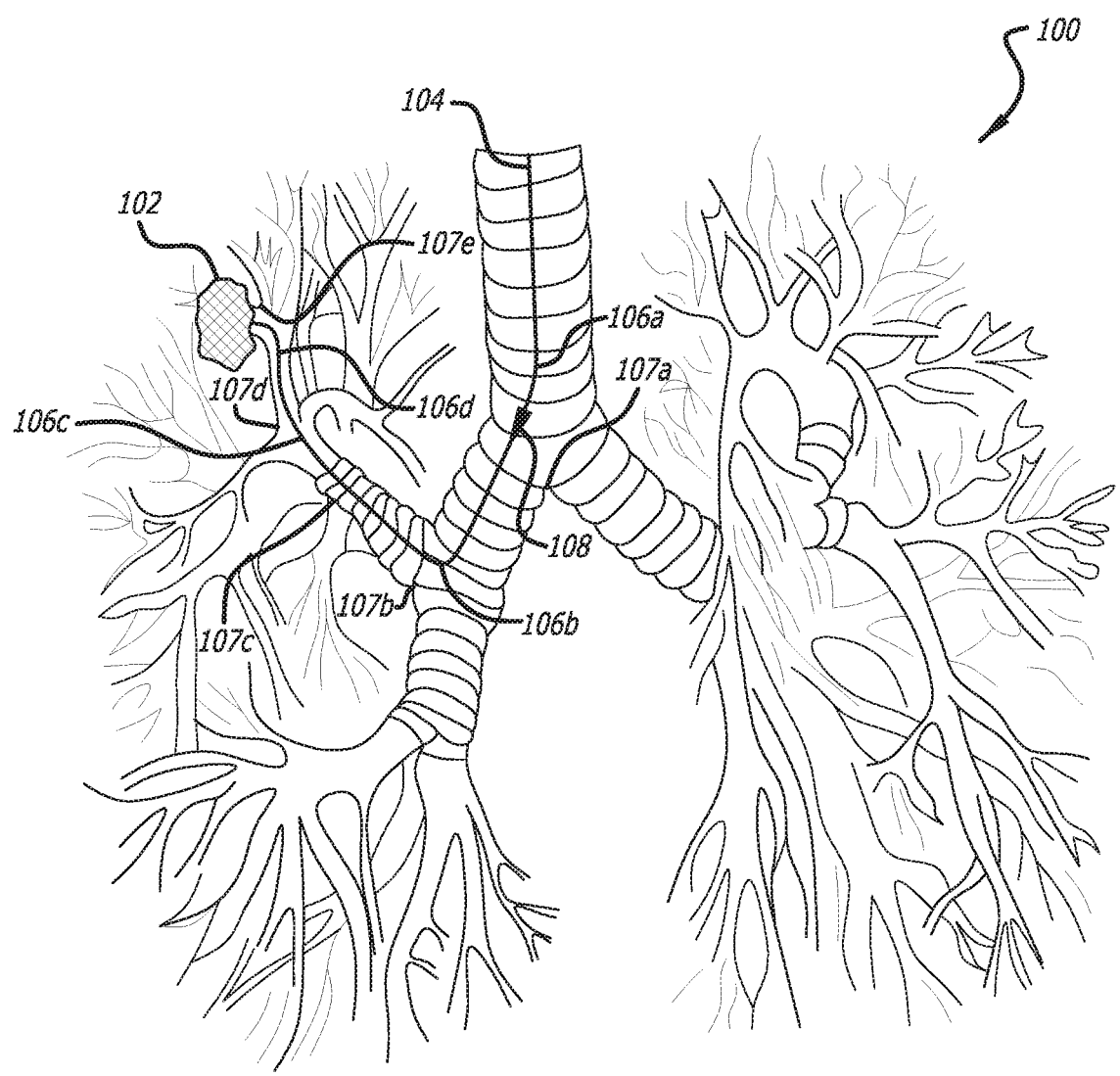

FIG. 5 shows that as the locatable guide is advanced the features of the bifurcation marked as landmark 107a grow larger, indicating that the locatable guide is nearing the waypoint 106a. The airway along the path remains highlighted to assist the physician in navigating to the lesion 102. Also, as seen in FIG. 6, the arrowhead 108 continues to advance along the path. It is envisioned that the arrowhead 108 may always be depicted along the desired path, thereby providing only an indication of how far along the path the locatable guide has been advance, or more preferably, the arrowhead may float independent of the path, thereby providing indication of the location of the locatable guide in the event that the physician has advanced the tip of the probe down an incorrect airway.

Figure 7:
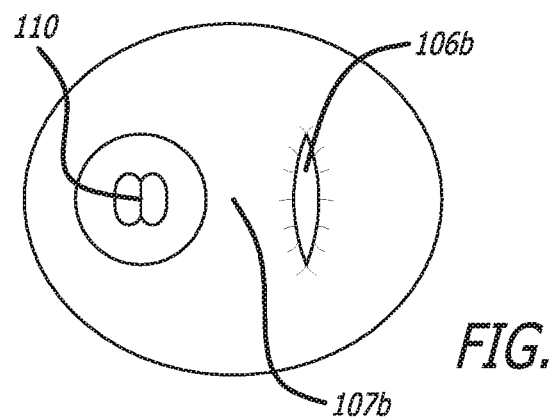
Figure 8:
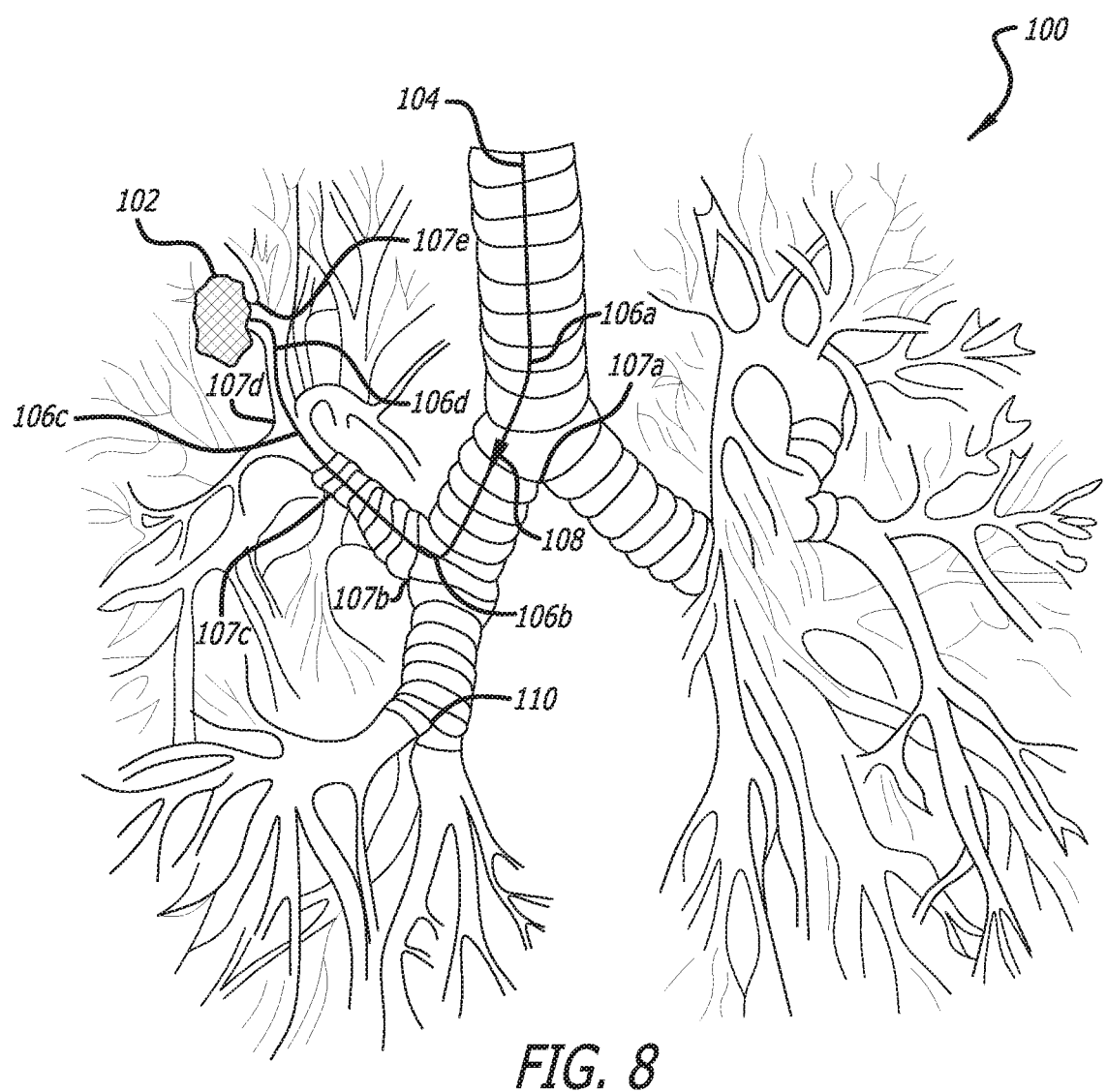

After the probe has passed through the opening of the correct airway, the view changes to that shown in FIG. 7, with the next waypoint 106b highlighted and an adjacent landmark 107b in the distant field view. Optionally, a more distant bifurcation 110 is depicted, giving depth to the perspective view of the airway. This bifurcation labeled for reference purposes in FIG. 8, which corresponds to the view in FIG. 7. The arrowhead 108 is still visible in FIG. 8 but has not advanced considerably past its position in FIG. 6, because crossing the threshold of a waypoint to a different view may be accomplished with a minute actual advancement of the locatable guide.

Figure 9:
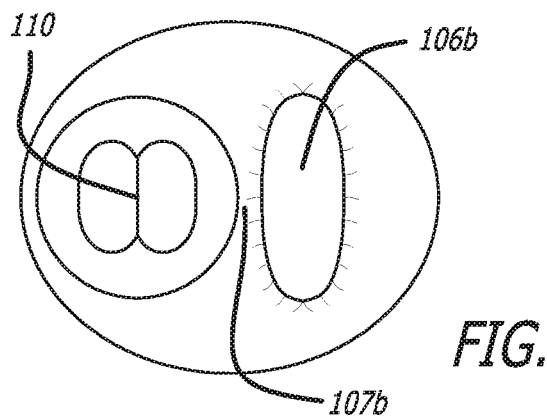
Figure 10:
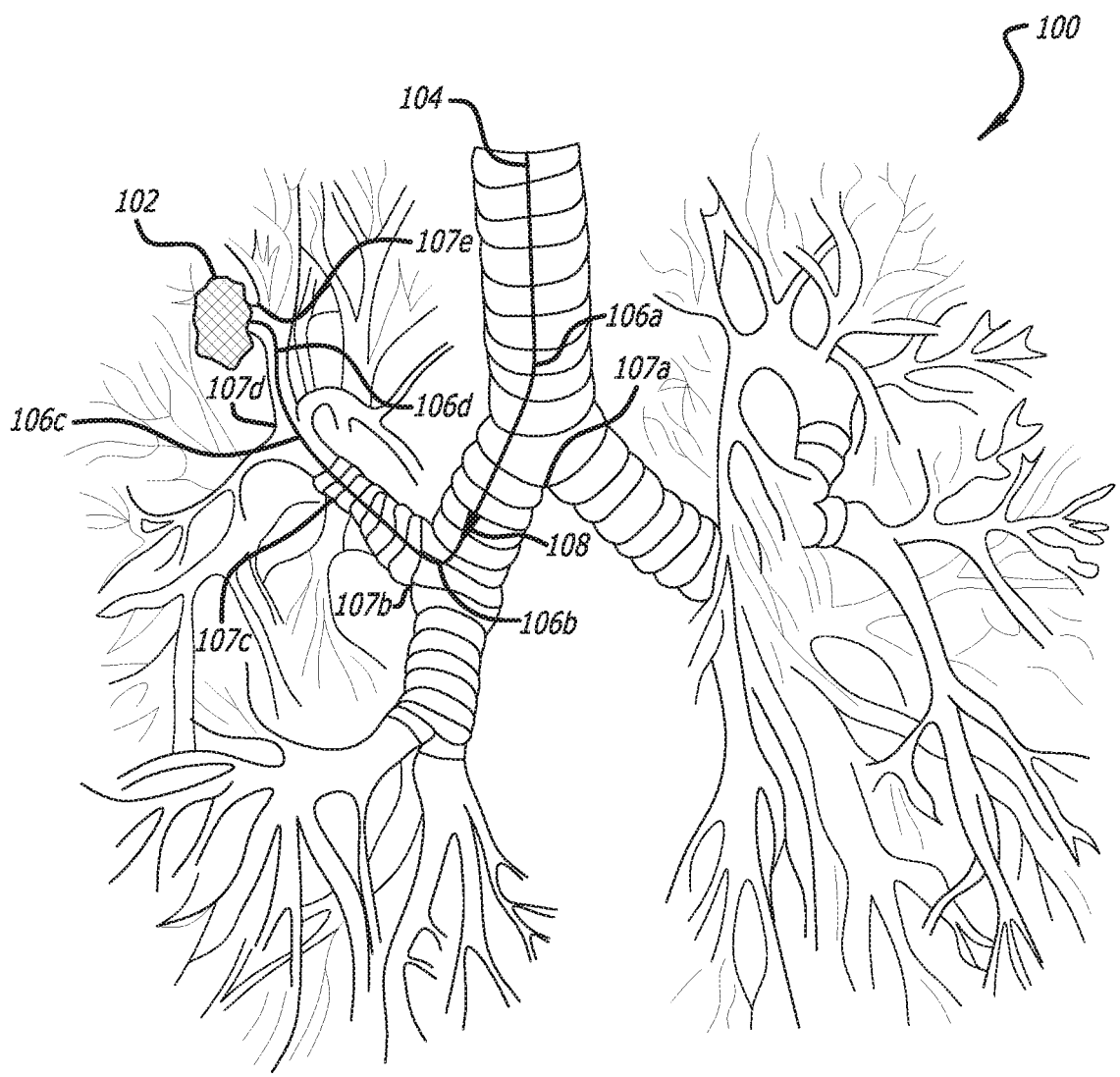

FIG. 9 shows the steady growth of the features 110, 107b and 106b as the locatable guide is advanced. FIG. 10 shows that the arrowhead 108 is close to approaching the waypoint 106b.

Figure 11:
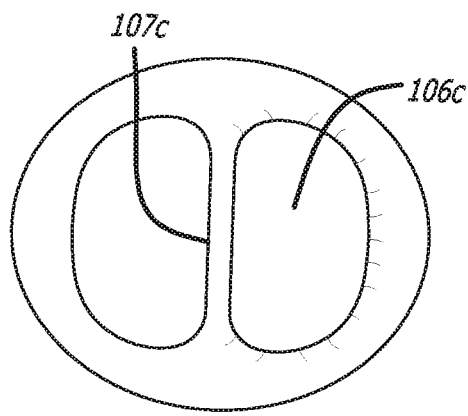
Figure 12:
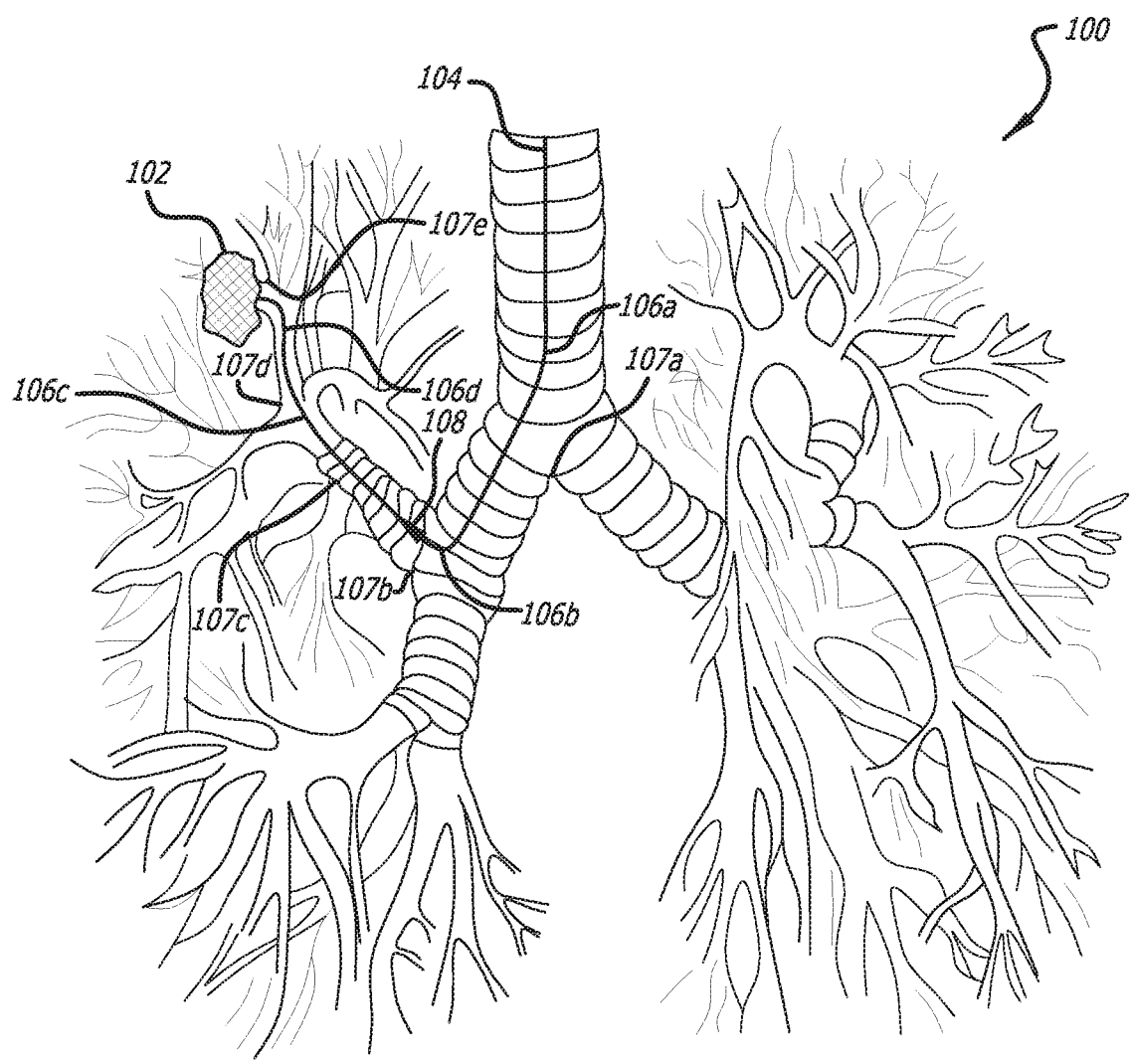

Upon passing waypoint 106b, the view changes to that shown in FIG. 11. Landmark 107c is visible with the correct airway containing waypoint 106c highlighted. FIG. 12 is the corresponding overview 100 with arrowhead 108 located just past waypoint 106b and pointing in the direction of the next waypoint 106c.

Figure 13:
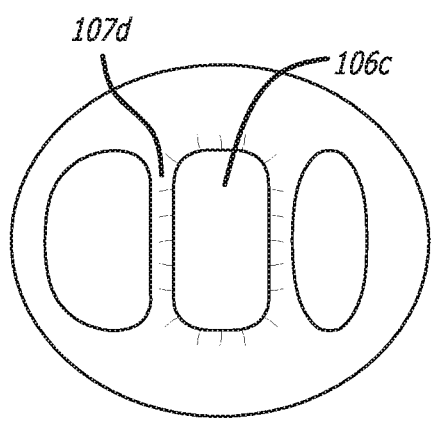

Upon passing landmark 107c, the view changes to that shown in FIG. 13. Landmark 107d is visible with the correct airway highlighted. Notably, waypoint 106c has not yet been reached and still appears in the distance. This illustrates that landmarks may be used as trigger points to update the views.

Figure 14:
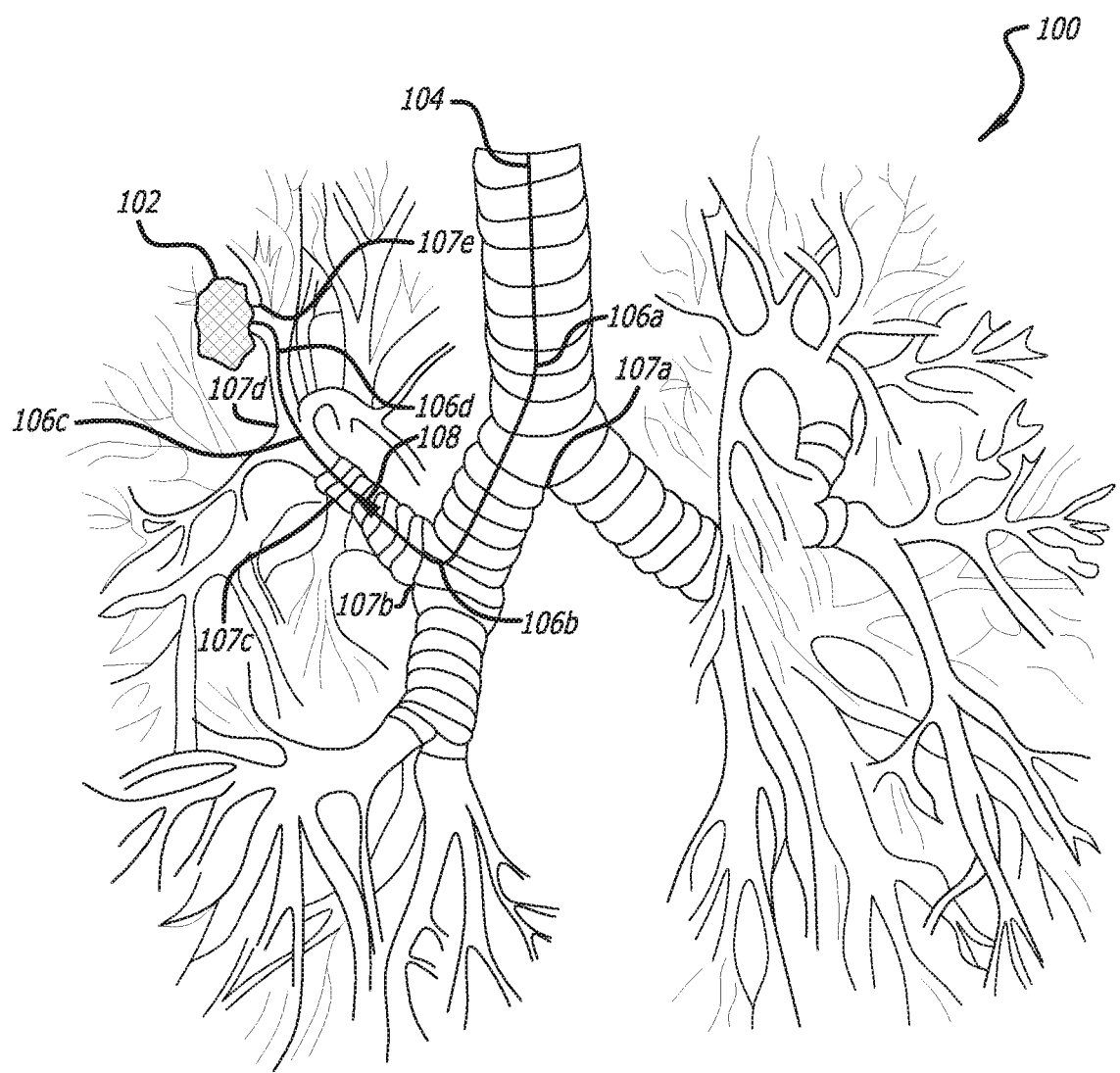

This is useful for long straight passages that result in passing several anatomical features. Alternatively, only waypoints may be used as trigger points. FIG. 14 shows that the arrowhead has advanced past waypoint 106c.

Figure 15:
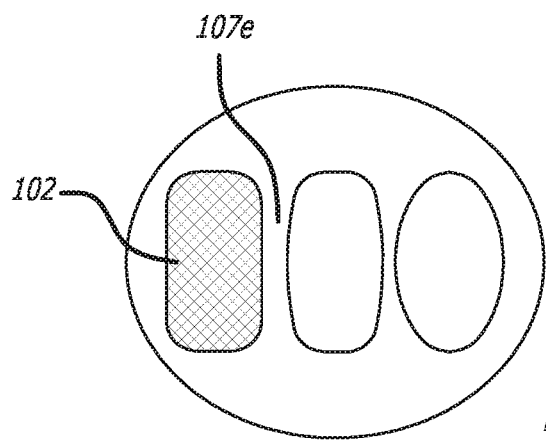
Figure 16:
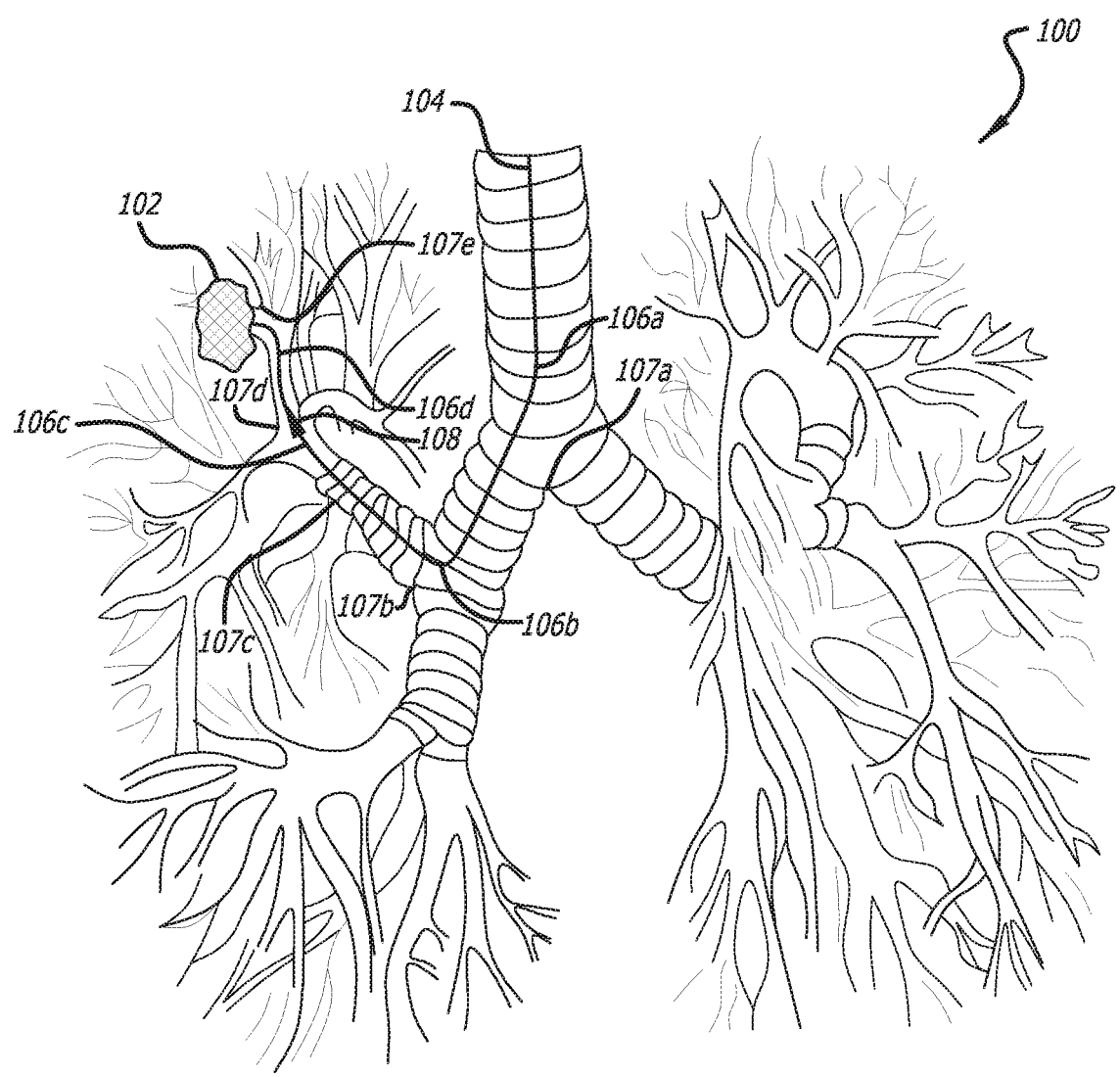

FIG. 15 provides the view after passing landmark 107d and corresponds with the overview 100 shown in FIG. 16. Optionally, the target 102, which is now visible, is highlighted in a different color or pattern than the various waypoints. It is also preferable to provide an indication when the tip of the probe is within an operational proximity to the target 102, such that the physician knows that the appropriate task (biopsy, ablation, excision, etc.) may be performed without further advancing or orienting the probe.

Another presentation embodiment is shown in FIGS. 17-22. In this embodiment, rather than indicating the advancement of the probe by producing a growing effect for the various features, a virtual image of the probe itself is provided and the viewpoint remains fixed just beyond each waypoint. Optionally, the physician may be given the option to advance the waypoint manually, in the event that two waypoints are spaced apart such that the image of the next waypoint is difficult to see.

Figure 17:
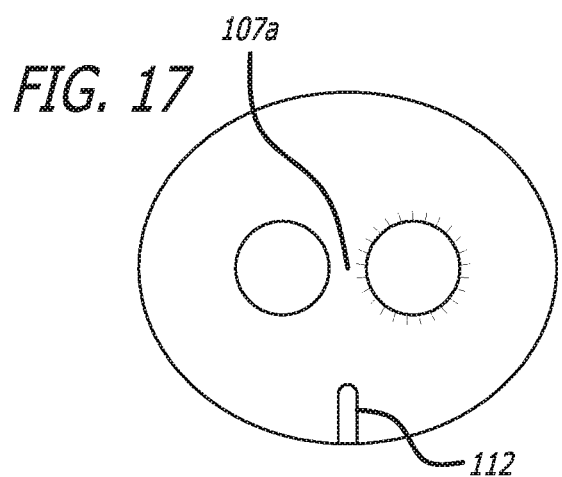

FIG. 17 shows the first landmark 107a and the tip of the locatable guide or probe 112. In order to ease navigation, the correct airway will be highlighted somehow, as shown. To further assist with navigation, the position of the locatable guide is shown as an arrowhead 108, or some other indication, on the overview 100 as shown in FIG. 4.

Figure 18:
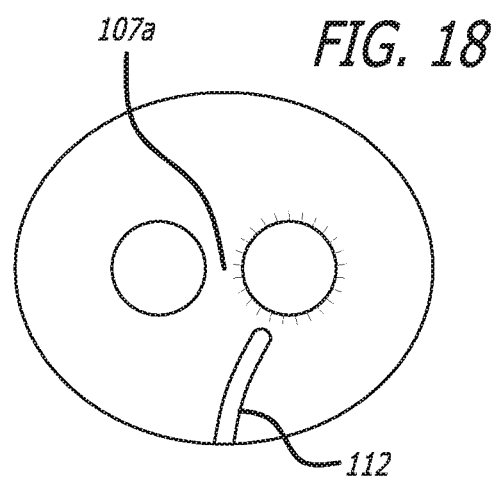
Figure 19:
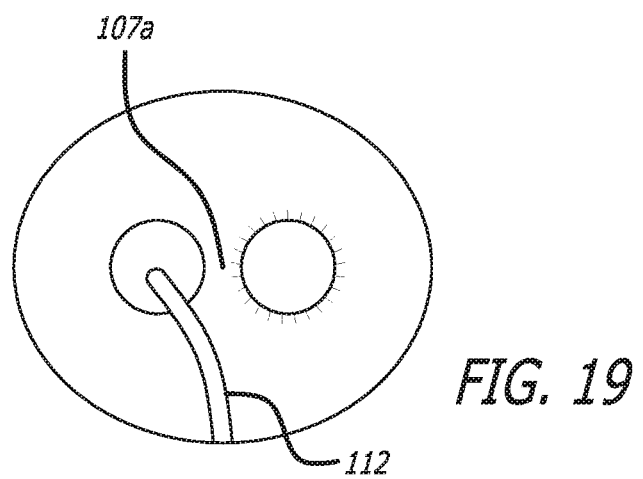

FIG. 18 shows that as the locatable guide is advanced the features of the bifurcation marked as landmark 107a remain the same size, but more of the probe 112 becomes visible, as though the probe 112 is advancing past and away from the viewpoint. The probe 112 is approaching the waypoint 106a and the physician can see that the probe 112 is turned toward the correct airway. Also, as seen in FIG. 6, the arrowhead 108 continues to advance along the path. It is envisioned that the arrowhead 108 may always be depicted along the desired path, thereby providing only an indication of how far along the path the locatable guide has been advance, or more preferably, the arrowhead may float independent of the path, thereby providing indication of the location of the locatable guide in the event that the physician has advanced the tip of the probe down an incorrect airway. Preferably, as shown in FIG. 19, in the event that the probe 112 is advanced down an incorrect airway, the viewpoint will not change to the next viewpoint. Rather, the probe 112 remains visible and is shown as advancing down the incorrect airway. This provides the physician with an easily understood indication that the probe should be retracted and advanced down the illuminated or highlighted airway. Preferably, the virtual probe 112 is constantly representative of the position and orientation of the actual probe.

Figure 20:
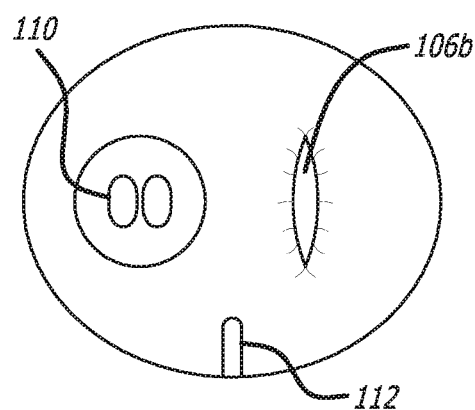

After the probe has passed through the opening of the correct airway, the view changes to that shown in FIG. 20, with the next waypoint 106b highlighted in the distant field view. Optionally, a more distant bifurcation 110 is depicted, giving depth to the perspective view of the airway. This bifurcation labeled for reference purposes in FIG. 8, which corresponds to the view in FIG. 20. The arrowhead 108 is still visible in FIG. 8 but has not advanced considerably past its position in FIG. 19, because crossing the threshold of a waypoint to a different view may be accomplished with a minute actual advancement of the locatable guide.

Figure 21:
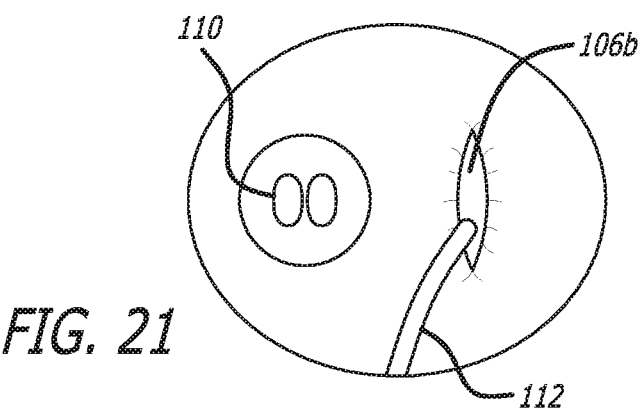

FIG. 21 shows the advancement of the probe 112 to a point where the probe may be steered toward the highlighted airway. Preferably, as the probe is steered, the virtual probe 112 is depicted as deflecting in the direction that the actual probe is deflected. FIG. 10 shows that the arrowhead 108 is close to approaching the waypoint 106b.

Figure 22:
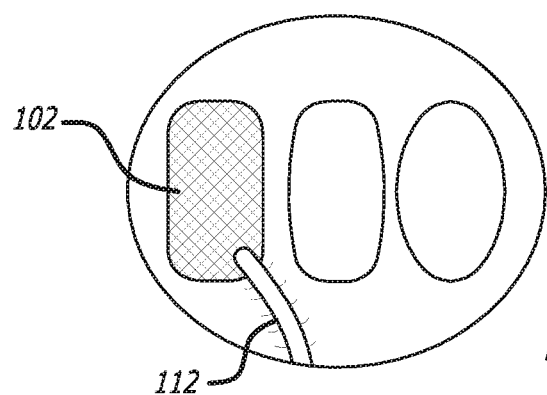

FIG. 22 provides the view after passing waypoint 106c and corresponds with the overview 100 shown in FIG. 16. Optionally, the target 102, which is now visible, is highlighted in a different color or pattern than the various waypoints. It is also preferable to provide an indication when the tip of the probe is within an operational proximity to the target 102, such that the physician knows that the appropriate task (biopsy, ablation, excision, etc.) may be performed without further advancing or orienting the probe. Alternatively, as shown in FIG. 22, the probe 112 itself is highlighted to show that the probe is in operational proximity to the target lesion 102.

Although the invention has been described in terms of particular embodiments and applications, one of ordinary skill in the art, in light of this teaching, can generate additional embodiments and modifications without departing from the spirit of or exceeding the scope of the claimed invention. For example, it is envisioned that the controlled perspective imaging method of the present invention could be used with a system that uses a navigation device other than a locatable guide, such as an optical navigation system. Using inputs such as identifiable landmarks and bronchoscope depth, through image processing the display method of the present invention could be utilized to provide a more user-friendly navigational interface. Accordingly, it is to be understood that the drawings and descriptions herein are proffered by way of example to facilitate comprehension of the invention and should not be construed to limit the scope thereof.

The invention claimed is:

1. A method of assisting navigation of a probe through a branched network of body lumens, comprising:
   monitoring movement of a probe using a three-dimensional tracking system; and
   displaying a user interface on a monitor, the user interface including:
      a computer-generated image of a distal portion of the probe and a virtual image of an interior of a lumen as seen from a viewpoint within the lumen;
   wherein:
      as the probe moves from a first location within the lumen to a second location within the lumen, the virtual image of the interior of the lumen changes and the computer-generated image of the distal portion of the probe remains fixed;
      as the probe moves from the second location within the lumen to an anatomical landmark, the virtual image of the interior of the lumen remains fixed and the computer-generated image of the distal portion of the probe changes; and
      when the probe arrives at the anatomical landmark within the lumen, the virtual image of the interior of the lumen changes to a different virtual image associated with the anatomical landmark, the different virtual image remaining fixed as the probe moves beyond the anatomical landmark.

2. The method of claim 1, wherein displaying a user interface on a monitor further includes illuminating a next lumen along a pathway to a target.

3. The method of claim 1, wherein displaying a user interface on a monitor further includes illuminating a target.

4. The method of claim 1, wherein displaying a user interface on a monitor further includes illuminating a waypoint.

5. The method of claim 1, wherein displaying a user interface on a monitor further includes displaying a schematic image of an interior of a lumen.

6. The method of claim 1, wherein displaying a user interface on a monitor further includes displaying a perspective image of an interior of a lumen.

7. The method of claim 1, wherein displaying a user interface on a monitor further includes displaying a parallel geometric image of an interior of a lumen.

8. The method of claim 1, further comprising displaying a second user interface on the monitor, the second user interface including an overview of the branched network of body lumens with an indication of a location of the probe thereon.

9. The method of claim 1, wherein monitoring movement of a probe using a three-dimensional tracking system includes monitoring movement of the probe using an electromagnetic tracking system.

10. The method of claim 1, further comprising:
defining a pathway to a target and a plurality of waypoints along the pathway; and
updating the viewpoint whenever the probe moves past one of the waypoints.

11. A system for navigating through a branched network of body lumens, comprising:
a control system configured to determine a position of a probe within the branched network; and
a monitor configured to display a user interface, the user interface including:
a computer-generated image of a distal portion of the probe and a virtual image of an interior of a lumen as seen from a viewpoint within the lumen; wherein:
as the probe moves from a first location within the lumen to a second location within the lumen, the virtual image of the interior of the lumen changes and the computer-generated image of the distal portion of the probe remains fixed;
as the probe moves from the second location within the lumen to an anatomical landmark, the virtual image of the interior of the lumen remains fixed and the computer-generated image of the distal portion of the probe changes; and
when the probe arrives at the anatomical landmark, the virtual image of the interior of the lumen changes to a different virtual image associated with the anatomical landmark, the different virtual image remaining fixed as the probe moves beyond the anatomical landmark.

12. The system of claim 11, wherein the user interface further includes an illuminated indication of a next lumen along a pathway to a target.

13. The system of claim 11, wherein the user interface further includes an illuminated target.

14. The system of claim 11, wherein the user interface further includes an illuminated waypoint.

15. The system of claim 11, wherein the user interface further includes a perspective view of the lumen.

16. The system of claim 11, wherein the user interface further includes a geometric parallel view of the lumen.

17. The system of claim 11, wherein the user interface further includes a computer-generated image of an overview of the branched network including an indication of a location of a distal tip of the probe.

18. A user interface for navigating through a branched network of lumens, the user interface comprising:
a computer-generated image of a distal portion of a probe and a virtual image of an interior of a lumen as seen from a viewpoint within the lumen; wherein:
as the probe moves from a first location within the lumen to a second location within the lumen, the virtual image of the interior of the lumen changes and the computer-generated image of the distal portion of the probe remains fixed;
as the probe moves from the second location within the lumen to an anatomical landmark, the virtual image of the interior of the lumen remains fixed and the computer-generated image of the distal portion of the probe changes; and
when the probe arrives at the anatomical landmark, the virtual image of the interior of the lumen changes to a different virtual image associated with the anatomical landmark, the different virtual image remaining fixed as the probe moves beyond the anatomical landmark.

19. The user interface of claim 18, further comprising an illuminated target.

20. The user interface of claim 18, further comprising an illuminated waypoint.

* * * * *